(12) United States Patent
Purea et al.

(10) Patent No.: US 10,120,044 B2
(45) Date of Patent: Nov. 6, 2018

(54) MICROWAVE COUPLER FOR OPTIMIZING A NMR PROBE HEAD FOR MAS-DNP

(71) Applicant: BRUKER BIOSPIN GMBH, Rheinstetten (DE)

(72) Inventors: Armin Purea, Bad Schoenborn (DE); Frank Engelke, Rheinstetten (DE); Alexander Krahn, Karlsruhe (DE)

(73) Assignee: Bruker BioSpin GmbH, Rheinstetten (DE)

( * ) Notice: Subject to any disclaimer, the term of this patent is extended or adjusted under 35 U.S.C. 154(b) by 387 days.

(21) Appl. No.: 14/910,706

(22) PCT Filed: Jul. 23, 2014

(86) PCT No.: PCT/EP2014/065826
§ 371 (c)(1),
(2) Date: Feb. 8, 2016

(87) PCT Pub. No.: WO2015/018640
PCT Pub. Date: Feb. 12, 2015

(65) Prior Publication Data
US 2016/0195593 A1 Jul. 7, 2016

(30) Foreign Application Priority Data
Aug. 9, 2013 (DE) ........................ 10 2013 215 782

(51) Int. Cl.
*G01R 33/345* (2006.01)
*G01R 33/28* (2006.01)
(Continued)

(52) U.S. Cl.
CPC ........... *G01R 33/345* (2013.01); *G01N 24/08* (2013.01); *G01R 33/282* (2013.01); *G01R 33/307* (2013.01); *G01R 33/62* (2013.01)

(58) Field of Classification Search
CPC .. G01R 33/345; G01R 33/282; G01R 33/307; G01R 33/62; G01N 24/08
See application file for complete search history.

(56) References Cited

U.S. PATENT DOCUMENTS

2007/0030005 A1* 2/2007 Krahn .................. G01R 33/307
324/321
2009/0230963 A1* 9/2009 Krahn .............. G01R 33/34046
324/318

FOREIGN PATENT DOCUMENTS

DE 10 2006 056 064 5/2008
JP 02182001 7/1990

OTHER PUBLICATIONS

Barnes, Alexander, et al. "Optimization of THz wave coupling . . . " Proceedings of the 2010 IEEE International Conference on Millimeter and Terahertz Waves: 1-3.*

(Continued)

*Primary Examiner* — G. M. A Hyder
(74) *Attorney, Agent, or Firm* — Paul Vincent

(57) ABSTRACT

An NMR DNP-MAS probe head (10) has an MAS stator (2) for receiving an MAS rotor (3) having a sample substance in a sample volume (4), and a hollow microwave waveguide (5)' for feeding microwave radiation through an opening (5a) of the microwave waveguide into the sample volume, an axially expanded rod-shaped microwave coupler (6) located in the opening made of dielectric material, characterized in that the microwave waveguide has a conically tapered hollow transition piece for coupling in an HE 11 mode, into which the microwave coupler projects at an all-round radial distance to the opening of the microwave waveguide. It is thus possible, in a surprisingly simple manner and by means of readily available technical means, (Continued)

to irradiate a considerably higher microwave energy in the HE 11 mode into the NMR measuring sample than by means of the known arrangements.

16 Claims, 6 Drawing Sheets

(51) Int. Cl.
  *G01R 33/30* (2006.01)
  *G01N 24/08* (2006.01)
  *G01R 33/62* (2006.01)

(56) References Cited

OTHER PUBLICATIONS

Melanie Rosay et al. "solid-state dynamic nuclear . . . " Phys. Chem Chem. Phys., 2010, 12 5850 5860.*

Barnes, Alexander et al., "Optimization of THz wave coupling . . . ", Proceedings of the 2010 IEEE International Conference on Millimeter and Terahertz Waves: 1-3.

Emilio A. Nanni et al., "Microwave field distribution . . . ", Journal of Magnetic Resonance 210 (2011) 16-23.

Bajaj V. et al., "Dynamice nuclear polarization . . . ", J Magn Reson 2003 160(2): 85-90.

L.R. Becerra et al., "A Spectrometer for Dynamic Nuclear . . . ", Journal of Magnetic Resonance, Series A 117, 28-40 (1995).

Vasyl Denysenkov et al., "Liquid state Dynamic Nuclear Polarization . . . ", Journal of Magnetic Resonance 217 (2012) 1-5.

Kevin J. Pike et al., "A spectrometer designed for 6.7 . . . ", Journal of Magnetic Resonance 215 (2012) 1-9.

Yoh Matsuki et al., "Dynamic nuclear polarization . . . ", Phys. Chem. Chem. Phys., 2010, 12, 5799 5803 / 5799.

Melanie Rosay et al., "Solid-state dynamic nuclear . . . ", Phys. Chem. Chem. Phys., 2010, 12, 5850 5860.

Manfred Thumm et al., "Design of Short . . . ", IEEE Transactions on Microwave Theory and Techniques 39 (Feb. 1991), No. 2.

Alexander B. Barnes et al., "Cryogenic sample exchange . . . ", Journal of Magnetic Resonance 198 (2009) 261-270.

Thorsten Maly et al., "Simplified THz Instrumentation . . . ", Appl Magn Reson (2012) 43:181-194.

* cited by examiner

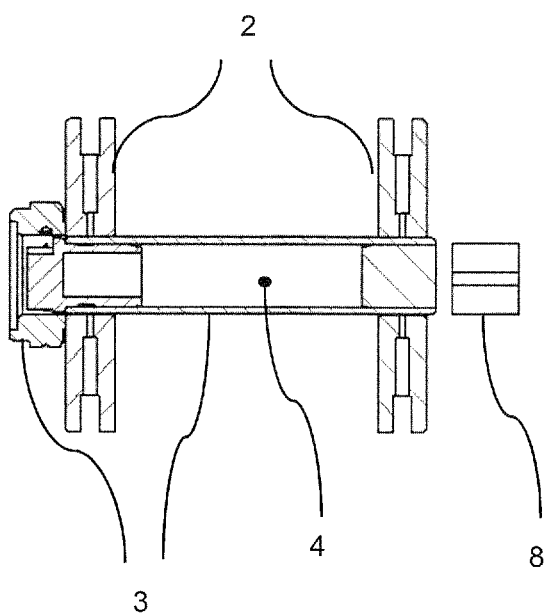
PRIOR ART    Fig. 6

MICROWAVE COUPLER FOR OPTIMIZING A NMR PROBE HEAD FOR MAS-DNP

This application is the national stage of PCT/EP2014/065826, filed on Jul. 23, 2014 and also claims Paris convention priority from DE 10 2013 215 782.7, filed Aug. 9, 2013, the entire disclosures of which are hereby incorporated by reference.

BACKGROUND OF THE INVENTION

The invention relates to an NMR (=nuclear magnetic resonance) DNP (=dynamic nuclear polarization)-MAS (=magic angle spinning) probe head comprising an MAS stator for receiving an MAS rotor having a sample substance in a sample volume, and a hollow microwave waveguide for feeding microwave radiation through an opening of the microwave waveguide into the sample volume, an axially expanded rod-shaped microwave coupler made of dielectric material and located in the opening of the microwave waveguide. In this context, "rod-shaped" means that the length in the rod axis is longer than the extent in the directions orthogonal thereto.

Such a configuration is known from DE 10 2008 009 376 A1 (=reference [0]). Reference [5] shows a similar configuration, but without an axially expanded rod-shaped microwave coupler made of dielectric material and located in the opening of the microwave waveguide.

Magnetic Nuclear Resonance with Magic Angle Spinning (=MAS-NMR)

In a magic angle spinning (MAS) device for performing experiments based on magnetic nuclear resonance (NMR), a sample to be examined is placed in a cylindrical MAS rotor inside an MAS stator and pneumatically made to rotate. NMR excitation and detection are performed in the normal way by means of a solenoid, into the center of which the rotor is inserted cylinder-symmetrically.

Dynamic Nuclear Polarization (=DNP)

In the field of nuclear magnetic resonance spectroscopy, there are experimental methods that enable a substantial increase in nuclear polarization and therefore in the detection sensitivity of the experiment. One of these methods is dynamic nuclear polarization (=DNP). This method requires simultaneous irradiation of a magnetic microwave field for polarization of electron spins at a frequency that is higher by a factor of 660 than the Larmor frequency of the 1 H nuclear spins.

A typical DNP arrangement consists of an NMR coil that is tuned to a nuclear Larmor frequency (e.g. $^1$H—400 MHz) and simultaneous irradiation of a microwave field at 263 GHz. DNP configurations are described in reference [7], for example.

MAS-DNP-NMR

When MAS-NMR is combined with dynamic nuclear polarization (DNP) to increase the signal, the sample must additionally be irradiated with an electromagnetic wave in the upper microwave/sub-THz range. This approach is described in references [2] to [6].

The microwave/sub-THz beam is guided along a microwave waveguide to the region of the sample and radiated onto the rotor and the sample through an open end either perpendicularly to the axis of the rotor (radial)—see references [3] to [5]—or parallel thereto (axial)—see references [2] and [6]. The spatial extent of the beam perpendicular to the direction of propagation is normally greater than the surface of the rotor, so that only part of the radiated energy is used for the DNP effect. In the case of radial irradiation, therefore, a change in the beam shape was achieved with a lens made of dielectric material that was better adapted to the cross-sectional area of the rotor—see references [1] and [3].

Because of the distance of the radiating waveguide aperture from the sample and the divergence of the microwave/sub-THz beam, the cross section of the beam at the sample location is substantially greater in at least one dimension than the cross section of the sample, so that the energy density at the sample location is reduced. There are also scattering effects of the beam at dielectric interfaces that can reduce the field strength further. In order to nevertheless produce the necessary field strength in the sample, a complex high-power microwave source has to be used—see references [4] to [6]. In the microwave coupler according to the reference cited above [0] (=DE 10 2008 009 376 A1), TE modes are to be coupled into the resonator. For this purpose, the microwave coupler is flush with the walls, which is physically necessary for this application. However, this is neither necessary nor helpful for coupling in the HE 11 mode.

The object of this invention is to provide an NMR DNP-MAS probe head of the type defined in the introduction, with which focused and therefore more efficient microwave irradiation into the sample volume is possible and in which the sample is polarized in the most homogeneous possible way, wherein, in particular, the HE 11 mode is to be optimally coupled.

SUMMARY OF THE INVENTION

This object is achieved in a surprisingly simple manner and by readily available technical means by an NMR DNP-MAS probe head having the characteristics stated in the introduction, characterized in that the microwave waveguide has a conically tapered hollow transition piece for coupling in an HE 11 mode, into which the microwave coupler projects at an all-round radial distance to the opening of the microwave waveguide.

Unlike the microwave coupler implemented flush with the walls according to reference [0], the essential aspect of this invention is that the rod-shaped microwave coupler is not connected flush with the walls of the microwave waveguide but is kept at a distance from the walls of the opening of the microwave waveguide by an all-round radial gap. This ensures that the desired HE 11 mode can be optimally coupled.

Due to the tapered cone of the hollow cylindrical microwave waveguide, the propagating wave can be focused onto a smaller extent. This makes it possible to achieve considerably more efficient coupling of the microwave beam into the sample volume. The rod-shaped coupler is used to concentrate the microwave field and to guide the beam directly to the sample volume.

In reference [0], tapered conical transitions are disclosed, but are geometrically at a different location and used for another purpose. The microwave coupler projects into the resonator in a similar configuration. In the microwave waveguide, however, the conical transition piece is outside. In this case, the direction plays an important role. With the device according to this invention, it is possible to capture the HE 11 mode, that is, a quasi-Gaussian mode, optimally, which is physically due, in particular, to the conical design in front of the coupling into the microwave coupler. No mode is coupled from the side, as shown in reference [0], but on the end face. In reference [0], the microwave coupler does not project into the conically tapered hollow transition piece, rather passes through it along the entire length. In reference [0], in contrast to this invention, coupling in of modes into a resonator is described. The aim is not simply to transport microwave power but to generate a standing wave in the relevant volume, into which a sample is then placed. In contrast thereto, the objective of this invention is to bring as much power as possible to the more remote MAS rotor. However, neither the rotor nor its immediate environment is intended to be a resonant structure. For this reason and because of the propagation characteristics, a Gaussian beam is most suitable, to which the entire design of the inventive device has also been adapted, because the HE 11 mode in free space becomes a Gaussian beam.

Unlike the standard probe head, by the inventive use of a rod-shaped microwave coupler, the cross section of the microwave beam can be adapted to the sample geometry, which significantly increases the energy density of the magnetic microwave field.

Such a design is useful, in particular, to polarize samples efficiently that are small relative to the beam cross section. For elongated samples, in particular, as they are typically used in MAS systems, homogeneous polarization along the entire length is achieved in conjunction with axial irradiation.

With the inventive probe head, compact solid-state microwave sources can be used because, due to the higher energy density, lower microwave power is required to generate a given field strength at the sample location.

In an especially preferred embodiment, the dimensions of the microwave coupler perpendicular to its rod axis are at least half the wavelength of the irradiated microwave radiation in the microwave coupler, except in possibly conical and/or funnel-shaped segments at the beginning and end of the microwave coupler. This ensures that the wave can be propagated in the coupler. Also preferred is an embodiment in which the microwave coupler is designed for a microwave frequency in the range 100-1000 GHz, wherein the minimum extent in the rod-shaped region of the microwave coupler is 0.15 mm/$\sqrt{\varepsilon_r}$-1.5 mm/$\sqrt{\varepsilon_r}$, wherein $\varepsilon_r$ is the relative permittivity of the material from which the microwave coupler is made. The dimensions are thus limited to the relevant values.

Embodiments of the inventive probe head are especially preferred in which the microwave coupler has at least one funnel-shaped and/or one conical and/or one stepped end. This optimizes coupling in and out.

In another advantageous embodiment of the inventive probe head, the microwave coupler has a cross-sectional profile that is constant in an axially central region. The microwave waveguide is cylindrically symmetrical. This symmetry is therefore continued in the microwave coupler to avoid a break in the symmetry.

In a preferred further variant of this embodiment, the cross-sectional profile of the microwave coupler is constant on its radially outer surface in an axially central region.

Embodiments of the inventive NMR probe head are highly advantageous in which the microwave waveguide is hollow and has periodic ribbing in the interior. This enables low-loss transmission with the HE 11 mode within the coupler.

One class of embodiments of the inventive NMR probe head is characterized in that the axis of the microwave coupler is disposed transversely, preferably perpendicularly to the axis of rotation of the MAS rotor. Due to the lateral, preferably radial direction of irradiation, the path of the wave through the rotor and sample is as short as possible.

In an alternate class of embodiments, the axis of the microwave coupler is disposed essentially parallel with the axis of rotation of the MAS rotor. Because of the direction of irradiation, the wave can be guided through the rotor.

These embodiments can be improved by variants, in which the axial end of the microwave coupler facing the sample volume is constituted as a base bearing of the MAS stator and is permanently connected thereto. In the case of axial irradiation, the base bearing is spatially disposed between the rotor/sample volume and the microwave waveguide. A coupler must then simultaneously perform the function of the base bearing to ensure that the performance of the MAS device is not impaired.

In a further advantageous embodiment of the inventive probe head, a mirror for reflecting the microwave radiation exiting the microwave coupler and penetrating through the sample volume is disposed on the side of the MAS stator that is opposite to the microwave coupler. Due to the reflection, the microwave radiation passes through the sample volume, not once but twice, which can result in an increase in the efficiency of transfer of the microwave radiation into the sample for the purpose of electron polarization.

Embodiments are especially preferred, in which a pneumatic sample changing system is provided for feeding and removing an MAS rotor to/from the MAS stator, as is described in detail in DE 10 2006 048 955 B4, for example.

Embodiments of the inventive probe head are also advantageous that are characterized in that the MAS stator is supported in a rotatable manner to set the MAS angle, such as is described in DE 10 2008 054 152 B3, for example.

In a highly preferred class of embodiments of the inventive probe head, at least one spacer made of dielectric material is provided between the microwave coupler and the microwave waveguide, which bridges a distance of at least one quarter of the wavelength of the microwave radiation to be coupled.

In advantageous variants of these embodiments, at least one spacer is constituted as a spacer ring, preferably as a multiplicity of spacer rings.

Alternatively or in addition, in variants, at least one spacer can also be constituted as a cap that can be plugged onto the microwave waveguide, into which the microwave coupler is integrated.

Finally, further advantageous embodiments of the inventive probe head are characterized in that the microwave coupler is made of non-magnetic, dielectric materials with a small loss angle (tan $\delta < 10^{-3}$), in particular, of PTFE or sapphire.

Further advantages of the invention result from the description and the drawing. Moreover, the features stated above and further below can be used singly or together in any combination according to the invention. The embodiments shown and described are not intended to be an exhaustive list, rather are examples to explain the invention.

The invention is shown in the drawing and is explained in more detail using embodiments. The figures show:

BRIEF DESCRIPTION OF THE DRAWING

FIG. 6 an MAS system according to prior art with an axial base bearing constituted as a Bernoulli bearing;

DESCRIPTION OF THE PREFERRED EMBODIMENT

Figure 1:
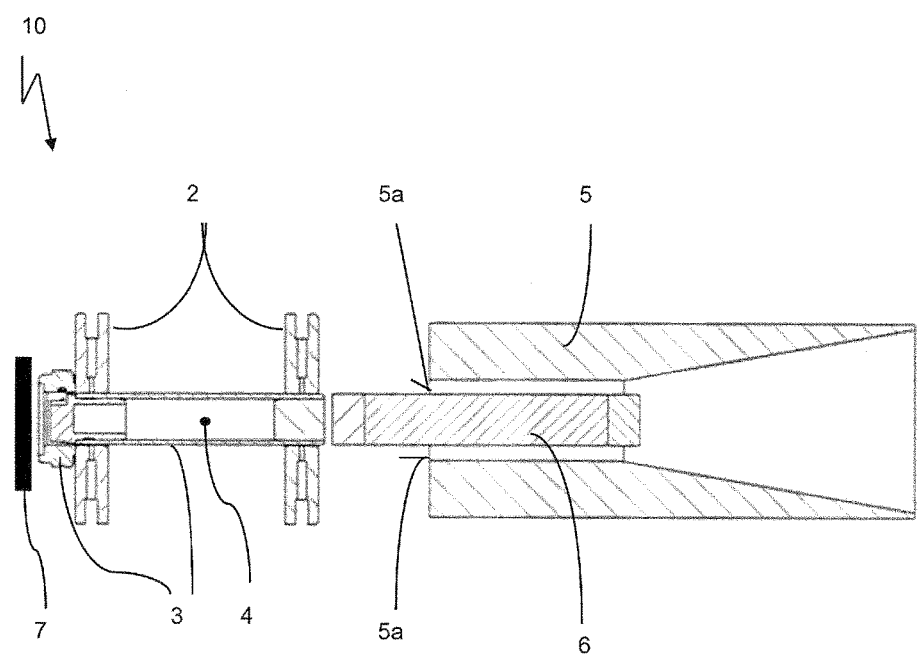
FIG. 1 a schematic longitudinal sectional view of an inventive NMR-MAS probe head with a microwave coupler projecting into the hollow end of a microwave waveguide in an axial configuration.

The invention relates to a new system for acquiring DNP MAS spectra in the field of NMR and comprises a NMR DNP-MAS probe head 10; 20 comprising a MAS stator 2 for receiving a MAS rotor 3 having a sample substance in a sample volume 4, and a hollow microwave waveguide 5 for feeding microwave radiation through an opening 5a of the microwave waveguide 5 into the sample volume 4. Unlike known devices, the invention is characterized in that an essentially rod-shaped microwave coupler 6; 6'; 6" extended along an axis and made of dielectric material is disposed in the opening 5a of the microwave waveguide.

A mirror 7; 7' for reflecting the microwave radiation exiting the microwave coupler 6; 6'; 6" and penetrating through the sample volume 4 is disposed on the side of the MAS stator 2 that is opposite to the microwave coupler 6; 6'; 6".

The main application of this invention is in the field of nuclear resonance spectroscopy (NMR) and preferably in the field of dynamic nuclear polarization (DNP).

To optimize the microwave/sub-THz beam, according to the invention a microwave coupler 6; 6'; 6" is to be used. This coupler has the function of capturing the intensity of a microwave beam incident upon the sample to be measured in HE 11 mode, guiding it, and emitting it again in a controlled manner. The microwave coupler can have a cylindrical, elliptical, or conical shape. It typically consists of a dielectric with negligible electrical conductivity ($<10^{-10}$ S/m).

This microwave coupler can be used in two different ways in connection with DNP MAS to increase the intensity of the microwave/sub-THz radiation at the sample location:

1. In the case of axial irradiation, the base bearing of the MAS stator 2 can be manufactured such that it is simultaneously used as a microwave coupler 6 for the purpose of this invention, and guides the incident microwave/sub-THz radiation into the MAS rotor 3 disposed inside the MAS stator 2. This configuration is shown in FIG. 1, wherein the MAS stator 2 is represented in the drawing only by its two air-bearing disks. In this embodiment, the base bearing and the end cap(s) of the rotor 3 are also part of the coupler 6.

Figure 2:
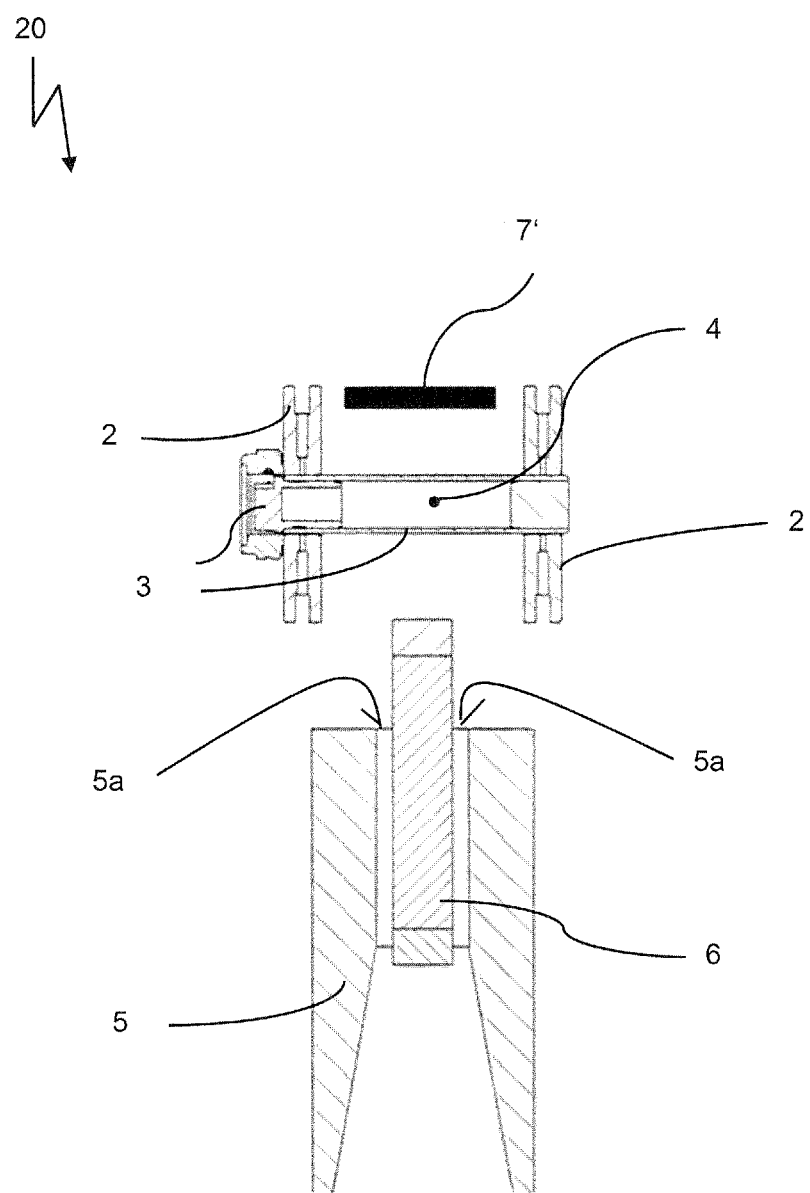
FIG. 2 like FIG. 1, but with a microwave waveguide disposed radially with respect to the rotor axis and a microwave coupler projecting into it.
Figure 3:
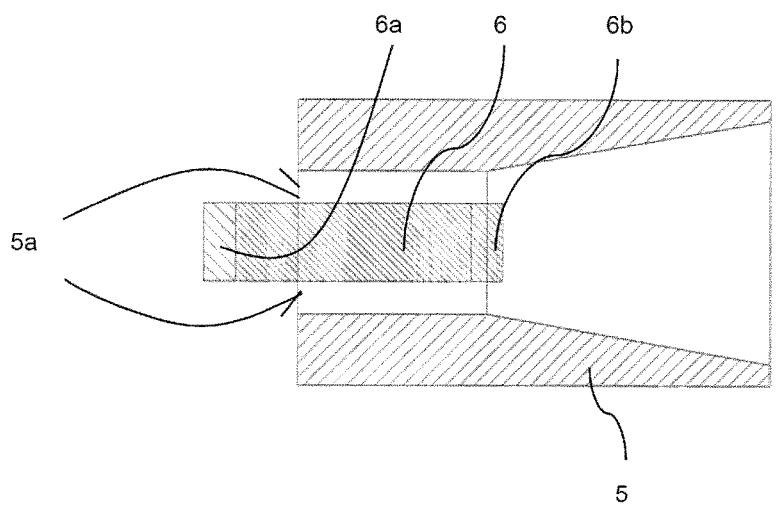
FIG. 3 a schematic detail view of a hollow microwave waveguide with a conically expanded hole at one end and a cylindrical microwave coupler projecting into it at the other end.

2. In the case of radial irradiation, the opening into the MAS stator 2 can be substantially smaller than the width of the incident microwave beam. In that case, the microwave coupler 6 can guide the beam in a concentrated fashion into the stator 2 and emit the microwave energy inside the stator 2 in a controlled manner, as is shown in FIG. 2. Both ends of the microwave coupler 6 can then be optimized so that as little beam intensity as possible is reflected. FIG. 3 shows in greater detail the inventively used hollow microwave waveguide 5 with a conically expanded hole at one end. A microwave coupler 6—having a cylindrical shape in the example shown here—projects into the opening 5a at the other end of the microwave waveguide 5. At the end projecting out of the opening 5a of the microwave waveguide 5, the coupler has a first end section 6a, which serves as the coupling region for focusing the radiated microwave energy onto the sample to be measured. The second end section 6b projecting into the microwave waveguide 5, on the other hand, marks a mode conversion region.

A microwave coupler that is typical of this invention comprises an approx. 5 mm long cylindrical dielectric with a diameter of 2 mm.

Each of the ends of the microwave coupler can have an at least stepped and/or conical and/or funnel-shaped end section 6a, 6b; 6a', 6b'; 6a", 6b" with a typical length of 3 mm.

Figure 4A:
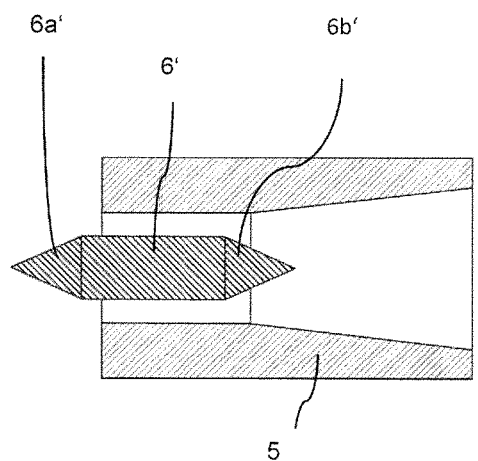
FIG. 4a like FIG. 3, but with a microwave coupler with both ends convexly conical.

FIG. 4a shows a microwave coupler 6'—usually preferred in practice—with end sections 6a', 6b' shaped conically convexly at both ends.

Figure 4B:
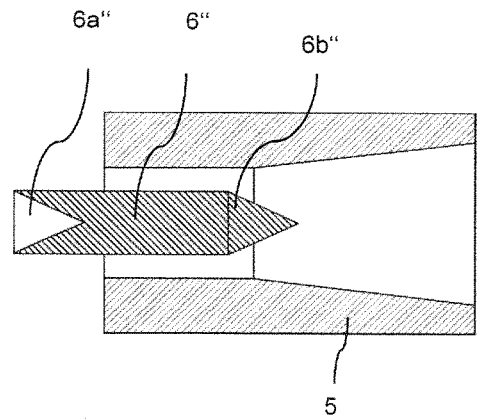
FIG. 4b like FIG. 4a, wherein the conical end of the microwave coupler projecting out of the microwave waveguide is concave.

FIG. 4b shows a microwave coupler 6" with a first end section 6a" shaped conically concavely and a—as in the embodiment according to FIG. 4a—second end section 6b" shaped conically convexly.

Figure 5A:
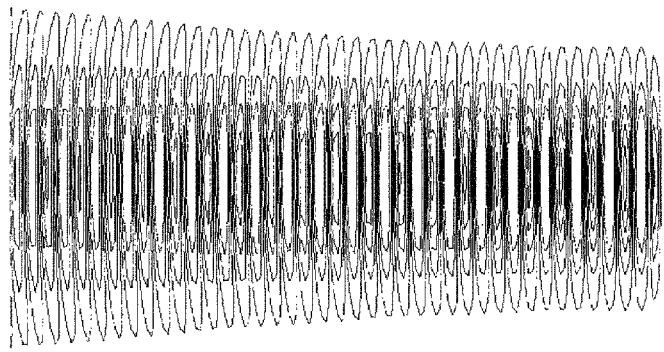
FIG. 5 an electromagnetic field simulation with the relevant calculated x-component of the E-field,
wherein
a) a field distribution with free propagation of the Gaussian microwave beam from the microwave waveguide without coupler and
b) a corresponding field distribution when a typical microwave coupler projecting into the microwave waveguide is used has been assumed.
Figure 5B:
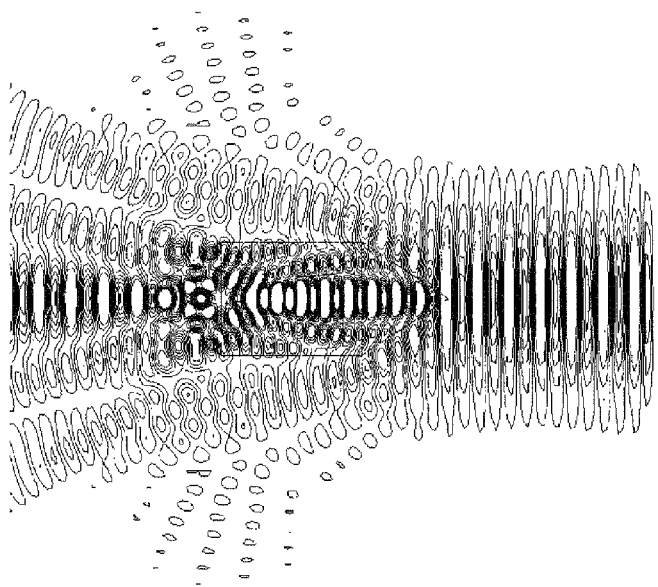

To illustrate the success of the inventive principle, two electromagnetic field simulations were performed and their results presented graphically in FIGS. 5a and 5b.

Specifically, FIG. 5a shows a field distribution with free propagation of the Gaussian microwave beam from the microwave waveguide without a coupler.

FIG. 5b graphically presents a corresponding field distribution in which the use of a microwave coupler projecting into the microwave waveguide was assumed in the simulation calculation. As can be clearly seen, the inventive use of a microwave coupler results in a considerable concentration of the microwave energy transmitted onto the sample to be measured.

The function of an inventive microwave coupler shown in FIGS. 5a and, above all, 5b with typical dimensions has been determined with the use of electromagnetic field simulation software (CST Microwave Studio 2012). A Gaussian beam (linear polarization, E-field in the x-direction) is propagated from the right-hand side in the left-hand direction (z-direction). The x-component of the E-field is shown in each case. The frequency of the beam is 263 GHz, that is, in the sub-THz range. The coupler is made of PTFE. The increased field amplitude in the region behind the coupler, in a spatially narrower band, can be seen.

Finally, for better comparison with this invention, FIG. 6 schematically shows a simple NMR DNP-MAS probe head configuration according to prior art with an MAS stator 2 for receiving an MAS rotor 3 with a sample substance in a sample volume 4. At the right-hand end of FIG. 6, a base bearing constituted as a Bernoulli bearing 8 is shown. The rotor-side end 6a; 6a'; 6a" of the microwave coupler 6; 6'; 6" of the inventive probe head 0; 20 is located at this position.

The microwave coupler 6; 6'; 6" is at a minimum radial distance from the microwave waveguide 5. The HE 11 mode from the microwave waveguide 5, to which coupling is performed, has a field profile (both E and H-Field) decaying toward the edge so that the major part of the microwave intensity is transmitted through the microwave coupler 6; 6'; 6". At the same time, the microwave coupler 6; 6'; 6" selects such a mode.

The minimum radial distance of the microwave coupler 6; 6'; 6" from the microwave waveguide 5 is one fourth of a wavelength or more, which is made possible by spacers made of dielectric material, which are thin relative to the wavelength, being less than a fourth of the wavelength.

Figure 7:
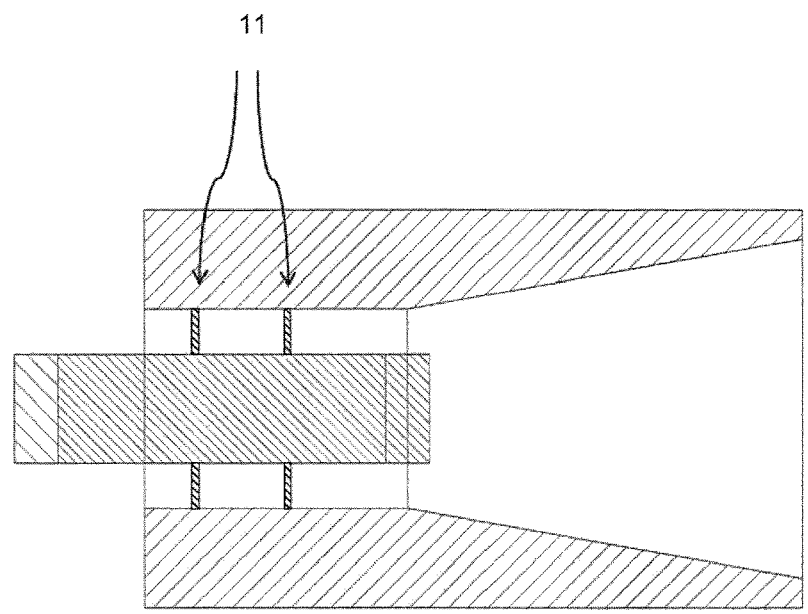
FIG. 7 a schematic longitudinal sectional view of the microwave coupler projecting into the hollow end of a microwave waveguide with spacer rings as a fastening variant.

Embodiments are possible as shown in FIG. 7 that have spacers 11 that are thin relative to the wavelength.

Figure 8:
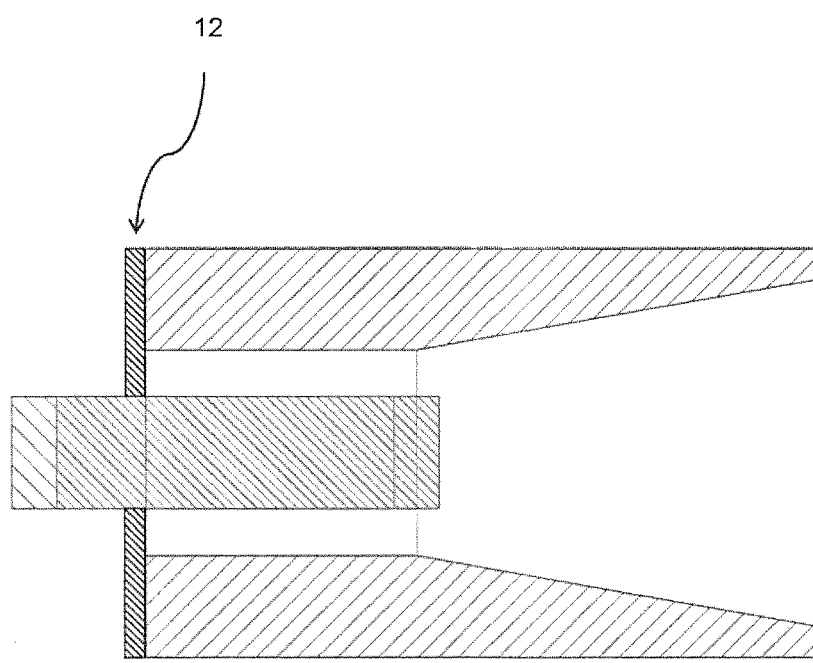
FIG. 8 a schematic longitudinal sectional view of the microwave coupler projecting into the hollow end of a microwave waveguide with a fastening variant in which the coupler is integrated into a plug-on cover cap.

As shown in FIG. 8, embodiments are also possible with the plug-on cap 12 that can be plugged onto the microwave waveguide 5, into which the microwave coupler 6; 6'; 6" is integrated.

Especially suitable for the microwave coupler 6; 6'; 6" are non-magnetic, dielectric materials with a small loss angle (tan δ<$10^{-3}$), for example, PTFE or sapphire.

Abbreviations

ESR electron spin resonance
(N)MR (nuclear) magnetic resonance
DNP dynamic nuclear polarization
MAS magic angle spinning
PBS photonic band-gap structure
hrNMR high resolution NMR
RF electromagnetic frequency range 1 MHz to 1000 MHz in NMR spectroscopy
THz terahertz, electromagnetic frequency range 0.3-3 THz.

LIST OF REFERENCES

[0] DE 10 2008 009 376 A1
[1] Barnes, Alexander et al.: "Optimization of THz wave coupling into samples in DNP/NMR spectroscopy." Proceedings of the 2010 IEEE International Conference on Millimeter and Terahertz Waves: 1-3.
[2] Matsuki et al.: "Dynamic nuclear polarization experiments at 14.1 T for solid-state NMR", PCCP 2010 (22), 5799-5803
[3] Nanni et al.: "Microwave Field Distribution in a Magic Angle Spinning Dynamic Nuclear Polarization NMR Probe", J Magn Reson. 2011 May; 210(1):16-23
[4] Bajaj V et al.: "Dynamic nuclear polarization at 9 T using a novel 250 GHz gyrotron microwave source", 3 Magn Reson 2003 160(2): 85-90
[5] M. Rosay et al.: "Solid-state dynamic nuclear polarization at 263 GHz: spectrometer design and experimental results", PCCP 2010 (22), 5850-5860
[6] Becerra et al.: "A Spectrometer for Dynamic Nuclear Polarization and Electron Paramagnetic Resonance at High Frequencies", 3 Magn Reson, A 1995, 1 17 (1): 28-40
[7] V. Denysenkov, Th. Prisner: "Liquid State Dynamic Nuclear Polarization probe with Fabry Perot resonator at 9.2 T", J. Magn. Reson. 217 (2012), 1-5

The invention claimed is:

1. An NMR (=nuclear magnetic resonance) DNP (=dynamic nuclear polarization)-MAS (=magic angle spinning) probe head for examination of a sample substance in a sample volume, the probe head comprising:
an MAS rotor structured for holding the sample substance;
an MAS stator structured for receiving said MAS rotor;
a hollow microwave waveguide having a conically tapered hollow transition piece structured for coupling in an HE 11 mode of microwave radiation and for passing said microwave radiation through an opening in said microwave waveguide into the sample volume; and
an axially extended rod-shaped microwave coupler made of dielectric material and disposed in said opening of said microwave waveguide, wherein said microwave coupler projects into said conically tapered, hollow transition piece and is disposed at an all-round radial distance to said opening of said microwave waveguide.

2. The probe head of claim 1, wherein dimensions of said microwave coupler perpendicular to a rod axis thereof are at least half a wavelength of irradiated microwave radiation in said microwave coupler.

3. The probe head of claim 1, wherein said microwave coupler is structured for a microwave frequency in a range of 100-1000 GHz, with a minimum extent in a rod-shaped region of said microwave coupler being 0.15 mm/$\sqrt{\varepsilon_r}$-1.5 mm/$\sqrt{\varepsilon_r}$, wherein $\varepsilon_r$ is a relative permittivity of a material from which said microwave coupler is made.

4. The probe head of claim 1, wherein said microwave coupler has at least one stepped, conical and/or funnel-shaped end section.

5. The probe head of claim 1, wherein said microwave coupler has a cross-sectional profile, which is constant in an axially central region.

6. The probe head of claim 1, wherein microwave coupler has a cross-sectional profile, which is constant in an axially central region said on a radially outer surface thereof in said axially central region.

7. The probe head of claim 1, wherein said microwave waveguide is hollow and has periodic ribbing in an interior thereof.

8. The probe head of claim 1, wherein an axis of said microwave coupler is disposed transversely or perpendicularly to an axis of rotation of said MAS rotor.

9. The probe head of claim 1, wherein an axis of said microwave coupler is disposed essentially parallel with an axis of rotation of said MAS rotor.

10. The probe head of claim 9, wherein an axial end of said microwave coupler facing the sample volume is constituted as a base bearing of said MAS stator and is permanently connected thereto.

11. The probe head of claim 10, wherein dimensions of said microwave coupler perpendicular to a rod axis thereof are at least half a wavelength of irradiated microwave radiation in said microwave coupler except at conical and/or funnel-shaped segments at a beginning and an end of said microwave coupler.

12. The probe head of claim 1, further comprising a mirror structured for reflecting microwave radiation exiting said microwave coupler and penetrating through the sample volume, wherein said mirror is disposed on a side of said MAS stator that is opposite to said microwave coupler.

13. The probe head of claim 1, further comprising at least one spacer made of dielectric material and disposed between said microwave coupler and said microwave waveguide to bridge a distance of at least one quarter of a wavelength of microwave radiation being coupled.

14. The probe head of claim 13, wherein at least one spacer is constituted as a spacer ring or as a multiplicity of spacer rings.

15. The probe head of claim 13, wherein at least one spacer is constituted as a cap plugged onto said microwave waveguide and into which said microwave coupler is integrated.

16. The probe head of claim 1, wherein said microwave coupler is made of non-magnetic dielectric materials with a small loss angle (tan $\delta < 10^{-3}$), is made of PTFE or is made of sapphire.

* * * * *